US005706809A

United States Patent [19]
Littmann et al.

[11] Patent Number: 5,706,809
[45] Date of Patent: Jan. 13, 1998

[54] METHOD AND SYSTEM FOR USING MULTIPLE INTRAVASCULAR SENSING DEVICES TO DETECT ELECTRICAL ACTIVITY

[75] Inventors: Laszlo Littmann, Charlotte, N.C.; Duane Dickens, San Clemente, Calif.

[73] Assignee: CaRDiMa, Inc., Fremont, Calif.

[21] Appl. No.: 188,298

[22] Filed: Jan. 27, 1994

Related U.S. Application Data

[63] Continuation-in-part of Ser. No. 10,818, Jan. 29, 1993, abandoned, Ser. No. 43,449, Apr. 5, 1993, abandoned, and Ser. No. 57,294, May 5, 1993, abandoned.

[51] Int. Cl.⁶ .................................................. A61B 5/042
[52] U.S. Cl. .................................................. 128/642
[58] Field of Search .................. 128/639, 642, 128/692, 693, 772; 607/116, 119, 122, 125, 123

[56] References Cited

U.S. PATENT DOCUMENTS

| Re. 33,925 | 5/1992 | Bales et al. | 606/48 |
|---|---|---|---|
| 452,220 | 5/1891 | Gunning | 607/116 |
| 4,271,847 | 6/1981 | Stokes | 607/122 |
| 4,402,330 | 9/1983 | Lindemans | 607/172 |
| 4,437,474 | 3/1984 | Peers-Trevarton | 607/119 |
| 4,458,677 | 7/1984 | McCorkle, Jr. | 607/125 |
| 4,467,817 | 8/1984 | Harris | 607/125 |
| 4,481,953 | 11/1984 | Gold et al. | 128/642 |
| 4,559,951 | 12/1985 | Dahl et al. | 128/642 |
| 4,690,155 | 9/1987 | Hess | 607/122 |
| 4,759,378 | 7/1988 | Swendson et al. | 607/122 |
| 4,777,955 | 10/1988 | Brayton et al. | |
| 4,785,815 | 11/1988 | Cohen et al. | 128/642 |
| 4,840,186 | 6/1989 | Lekholm et al. | 128/784 |
| 4,867,173 | 9/1989 | Leoni | 128/772 |
| 4,869,248 | 9/1989 | Narula | 128/303.13 |
| 4,945,912 | 8/1990 | Langberg | 128/642 |
| 4,957,110 | 9/1990 | Vogel et al. | 128/642 |
| 4,966,597 | 10/1990 | Cosman | 606/50 |
| 4,979,510 | 12/1990 | Franz et al. | 128/642 |
| 5,029,585 | 7/1991 | Lieber et al. | 607/125 |

(List continued on next page.)

FOREIGN PATENT DOCUMENTS

| 0293499 | 7/1988 | European Pat. Off. | 607/116 |
|---|---|---|---|
| 1813232 | 6/1969 | Germany | 607/116 |
| 2605590 | 8/1977 | Germany | 607/123 |
| 3718139C1 | 12/1988 | Germany . | |
| WO 80/02801 | 12/1989 | WIPO . | |
| WO 90/03151 | 4/1990 | WIPO . | |
| WO 92/21278 | 12/1992 | WIPO . | |
| WO 94/06349 | 3/1994 | WIPO . | |

OTHER PUBLICATIONS

Lawrence T. Weston, M.D., et al., "A Prototype Coronary Electrode Catheter for Intracoronary Electrogram Recording," *The American Journal of Cardiology*, vol. 70, Dec. 1, 1992, pp. 1492 and 1493.

Repetto, et al., Transcoronary Epicardial Mapping of Accessory Pathways. Implications for Ablation Techniques. 10th Int'l Cong., "The New Frontiers of Arrhythmias." Marilleva, Italy. Jan. 25–Feb. 1, 1992. pp. 475–480.

(List continued on next page.)

*Primary Examiner*—Lee S. Cohen
*Attorney, Agent, or Firm*—Heller Ehrman White & McAuliffe

[57] ABSTRACT

A method and system for detecting electrical activity within a patient's heart, particularly the electrical activity which causes arrhythmia, which includes a first intravascular device such as a catheter or guidewire having a plurality of sensing electrodes on a distal portion thereof which is disposed within one location of the patient's coronary vasculature and a second intravascular device such as a catheter or guidewire having a plurality of sensing electrodes on a distal portion thereof which is disposed within a second location of the patient's coronary vasculature to facilitate mapping the electrical activity of the patient's heart. Once the electrical activity has been mapped, therapeutic procedures can be initiated.

31 Claims, 8 Drawing Sheets

U.S. PATENT DOCUMENTS

| | | | |
|---|---|---|---|
| 5,044,375 | 9/1991 | Bach, Jr. et al. | 128/786 |
| 5,056,517 | 10/1991 | Fenici etal. | 128/419 |
| 5,083,565 | 1/1992 | Parins | 128/642 |
| 5,095,916 | 3/1992 | Smits | 607/119 |
| 5,095,917 | 3/1992 | Vancaillie | 128/831 |
| 5,099,838 | 3/1992 | Bardy . | |
| 5,122,136 | 6/1992 | Guleilmi et al. | 606/32 |
| 5,125,896 | 6/1992 | Hojeibane . | |
| 5,140,987 | 8/1992 | Schuger et al. . | |
| 5,163,445 | 11/1992 | Christian et al. | 607/116 |
| 5,165,403 | 11/1992 | Mehra . | |
| 5,170,802 | 12/1992 | Mehra . | |
| 5,174,288 | 12/1992 | Bardy et al. | 128/419 D |
| 5,184,621 | 2/1993 | Vogel et al. | 128/642 |
| 5,193,546 | 3/1993 | Vogel et al. . | |
| 5,193,550 | 3/1993 | Duffin | 128/697 |
| 5,330,522 | 7/1994 | Kreyenhagen | 607/122 |

OTHER PUBLICATIONS

Lesh, M.D., et al., Mapping in the Right Coronary Artery as an Aid to Radiofrequency ablation of Right–Sided Accessory Pathways. NASPE Abstracts. *PACE*, vol. 14, Apr. 1991, Part II, p. 671, Abstract 213.

Swartz, M.D., et al., Endocardial Atrial Catheter Ablation of Accessory Pathways After Intravascular Localization. NASPE Abstracts, *PACE*, vol. 13, Apr. 1990, p. 527, Abstract 126.

Fisher et al., "Nonsurgical Electrical Ablation of Tachycardias: Importance of Prior in Vitro Testing of Catheter Leads," *PACE* (1984) 7:74–81.

Brugada, et al., "Termination of Tachycardias by Interrupting Blood Flow to the Arrhythmogenic Area," *Am. J. Cardiology* (1988) 62:387–392.

Walter, et al., Europ. Surg. Res. 3:130–138 (1971).

Brugada, et al., "Transcordary Chemical Ablation of Ventricular Tachycardia," *Circulation* (1989) 79:475–482.

METHOD AND SYSTEM FOR USING MULTIPLE INTRAVASCULAR SENSING DEVICES TO DETECT ELECTRICAL ACTIVITY

RELATED APPLICATIONS

This application is a continuation-in-part application of application Ser. No. 08/010,818, filed Jan. 29, 1993, now abandoned, application Ser. No. 08/043,449, filed Apr. 5, 1993, now abandoned, and application Ser. No. 08/057,294, filed May 5, 1993, now abandoned, which are incorporated herein in their entirety by reference.

BACKGROUND OF THE INVENTION

This invention generally relates to the detection of electrical activity or signals within a patient's heart and particularly for determining the source of signals causing arrhythmia.

Prior methods for treating a patient's arrhythmia include the use of antiarrhythmic drugs such as sodium and calcium channel blockers or drugs which reduce the Beta-adrenergic activity. Other methods include the surgically sectioning the origin of the signals causing the arrhythmia or the conducting pathway for such signals. More frequently, however, to terminate the arrhythmia, the arrhythmogenic site which causes the arrhythmia is destroyed by heat, e.g. applying a laser beam or radio frequency (RF) energy to a desired location on the patient's endocardium.

In the latter instance, the location of the site causing the arrhythmia must be accurately known in order to be able to contact the desired location with a tissue destroying device. A major problem of ablating the arrhythmogenic site, a conductive pathway or a re-entry site is to accurately determine the location and size of the site so that an excessive amount of good tissue is not destroyed adjacent the site to ensure that the arrhythmia does not return. For example, the average arrhythmogenic site consists of about 1.4 $cm^2$ of endocardial tissue, whereas a re-entrant site might be much larger. RF ablation techniques produce lesions about 0.5 $cm^2$ in diameter, so a number of lesions may have to be generated in order to completely ablate the area of interest. If the site is not accurately mapped, much of the good tissue surrounding the site will be unnecessarily destroyed.

A variety of methods have been used to detect electrical activity within a patient's heart to facilitate the mapping of such heart signals and to thereby determine the location of the electrical signals causing the arrhythmia.

A number of U.S. Patents describe the use of elongated intravascular signal sensing devices which are advanced through the patient's vasculature until the distal portion having sensing electrodes is disposed within one of the heart chambers with the electrodes in contact with the endocardial lining. While this procedure is widely used, it does not always allow the site of arrhythmogenic signals to be accurately determined.

The literature also mentions advancing an intravascular signal sensing device within a patient's coronary artery or coronary sinus or a cardiac vein. However, these methods have been clinical experiment and have not been widely employed.

What has been needed is a method and system for accurately detecting the source of signals which cause the arrhythmia.

SUMMARY OF THE INVENTION

This invention is directed to a method and system for detecting electrical activity from several intravascular locations within a patient's heart to facilitate accurate determination of the site of such electrical activity.

In accordance with one embodiment of the invention, a plurality of intravascular devices are positioned within the coronary arteries and/or cardiac veins of a patient's heart to detect electrical activity. Each of the intravascular devices include an elongated shaft with a proximal section and a distal section with a plurality of sensing electrodes preferably adapted for a bipolar mode of operation spaced along a length of the distal section. Up to 20 or more bipolar electrode pairs may be provided along the distal section of the shaft. The distal section of the shaft is configured so as to be considerably more flexible than the proximal section and to be advanceable through a patient's coronary anatomy. The sensing electrodes are electrically connected to electrical conductors which extend from the proximal end of the shaft to the distal section where the electrodes are located.

The shaft is preferably formed of a plurality of insulated electrical conductors braided or wound into an elongated tubular member, although not all of the strands which make up the tubular member need be electrical conductors. The insulation on a separate individual conductor is exposed under each of the individual electrodes so that an electrical connection can be made between each of the electrodes and a separate electrical conductor. The electrical connection may be secured by means of a suitable solder or brazing material. The electrodes are secured to the underlying tubular member by a suitable means such as an adhesive so as to ensure that appropriate electrical contact with the exposed conductors is maintained even though brazed or soldered.

The elongated intravascular sensing devices of the invention may be in the form of a guidewire or a catheter. The guidewire in one embodiment generally has an elongated core member which is disposed within tubular member formed by the braided electrical conductors. The distal section of the guidewire has a flexible tip coil which is distal to the length on which the electrodes extend and which is disposed about the distal extremity of the core member. The distal end of the core member may be manually shapable by the physician to facilitate steerability by torquing the proximal end. A smooth rounded tip is provided at the distal end of the coil to avoid damage when being advanced through the patient's vasculature. A safety or shaping ribbon may extend from the distal end of the core member to the rounded tip in conventional guidewire fashion to facilitate shaping and to prevent the loss of the distal tip of the guidewire.

In another presently preferred embodiment, the elongated sensing device may be in the form of a catheter which has an elongated inner lumen extending from the proximal end to a discharge or guidewire port in the distal end of the device. The distal end of the catheter may be provided with a soft tip to minimize traumatic engagement with a blood vessel wall when being advanced therein. The inner lumen of the catheter form of the device is usually configured to facilitate the slidable disposition of a guidewire version of the device of the invention therein which allows signal detection at separate locations within the same blood vessel or branch thereof.

In one presently preferred embodiment, at least two elongated intravascular devices are advanced into separate blood vessels of a patient's heart in order to detect electrical activity in two intravascular locations. In this embodiment the devices may be guidewires or catheters with inner lumens adapted to receive guidewires. The positions of the intravascular sensing devices may be adjusted within the individual blood vessels to optimize the reception of the electrical activity to provide a greater degree of accuracy in detecting the ectopic foci.

In another presently preferred embodiment, at least one of the elongated intravascular devices is a catheter with an inner lumen extending therein and at least one of the elongated intravascular devices is a guidewire which is configured to be slidably received within the inner lumen of the catheter and extend out the guidewire port in the distal end of the catheter. Electrical activity is detected at multiple locations within a single blood vessel or branch thereof by means of the electrodes on the catheter and the electrodes on the guidewire. After the electrical activity is detected at a first location, the relative positions of the catheter and the guidewire disposed within the inner lumen of the catheter may be adjusted and then electrical activity may be detected again. Detections of electrical activity may be repeated at several other locations within the same coronary artery or cardiac vein or elsewhere in the vasculature of the patient's heart to pin point the arrhythmogenic site.

The sensing electrodes on the intravascular devices of the present invention are preferably circular bands about 0.25 to about 1 mm in width and may be made from conducting material which is biocompatible with the body fluids such as gold. The electrodes are preferably grouped in electrode pairs which are spaced from each other by about 0.5 to about 2 mm, preferably about 0.75 to about 1.25 mm, and the spacing between the bipolar electrode pairs should be about 1 to about 10 mm, preferably about 6 to about 8 mm.

A plastic jacket, preferably a lubricous polymer such as a thermoplastic fluoropolymer, is applied to the length of the shaft of the intravascular sensing device with a slight overlap of the jacket over the edges of the individual electrodes to prevent exposure of a sharp metallic edge which can cause damage when advanced through blood vessels.

When using the intravascular system of the invention, the plurality of devices are first introduced into the patient percutaneously or by means of a cut-down into one or more of the patient's major peripheral arteries or veins (e.g. the femoral vein or artery) and advanced through the vasculature to one or more desired locations within the veins or arteries of the patient's heart. The distal section of the elongated devices of the invention is preferably configured to be advanceable within blood vessels having native inner diameters of less than about one mm and frequently having native diameters smaller than 0.75 mm.

Electrical activity from the patient's heart is received by the electrodes on the intravascular devices and transmitted through the electrical conductors attached to the individual electrodes to multipin connectors on the proximal ends of these devices. In a presently preferred method of using the elongated devices of the invention, a plurality of elongated devices are employed, with the individual devices being advanced into the arteries and/or veins of the patient's heart which may be branched from major arteries or veins. In many instances it is desirable to provide a device within the patient's heart chambers with electrodes to provide known pacing signals to the endocardium which can be compared with the signals received by one or more intravascular sensing devices within epicardial blood vessels. This greatly facilitates the detection of the site of an arrhythmogenic source or a conductive pathway, particularly within the ventricular region of the patient's heart.

These and other advantages will become more apparent from the following detailed description of the invention and the accompanying exemplary drawings.

DETAILED DESCRIPTION OF THE INVENTION

Figure 1:
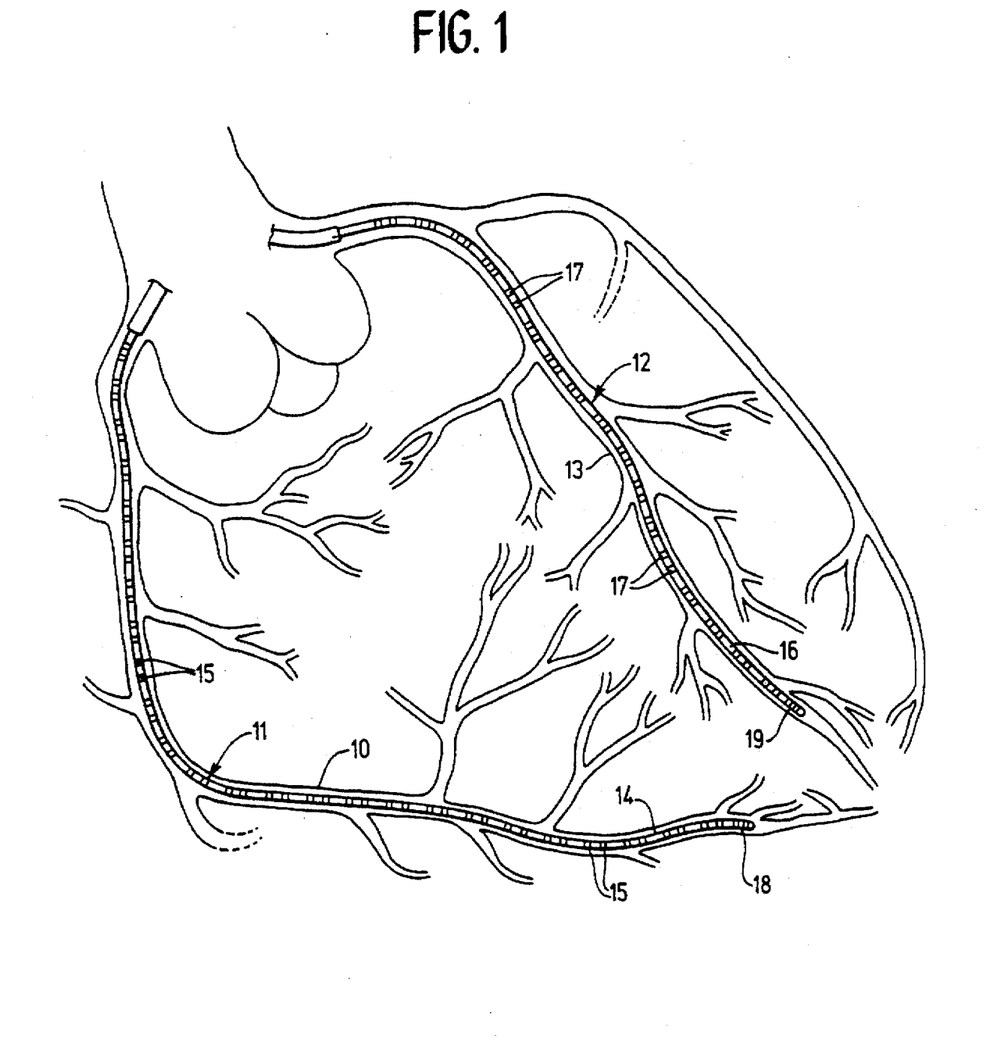
FIG. 1 is an anterior view of the coronary arteries of a human heart with portions of the right coronary artery and the anterior interventricular branch of the left coronary artery in section to illustrate the intravascular devices therein.

One presently preferred method of the invention is shown in FIG. 1 wherein a first elongated intravascular sensing device 10 is disposed within the right coronary artery 11 and a second elongated intravascular sensing device 12 is disposed within the anterior interventricular branch of the left coronary artery 13. As shown, the distal portion 14 of the first elongated intravascular device 10, having a plurality of electrodes 15, extends along a major portion of the right coronary artery 11 and the distal portion 16 of the second elongated intravascular sensing device 11, having a plurality of electrodes 17, extends along a major portion of the anterior interventricular branch of the left coronary artery 13. The individual intravascular devices 10 and 12 may be moved within the arteries as needed to optimize the signals received and particularly to detect with some precision the first onset of signals in question in order to more accurately pin point the source thereof. The intravascular sensing devices 10 and 12 as shown are in the form of guidewires which have shapable distal tips 18 and 19 to facilitate entry into side branches of the patient's epicardial blood vessels.

Figure 2:
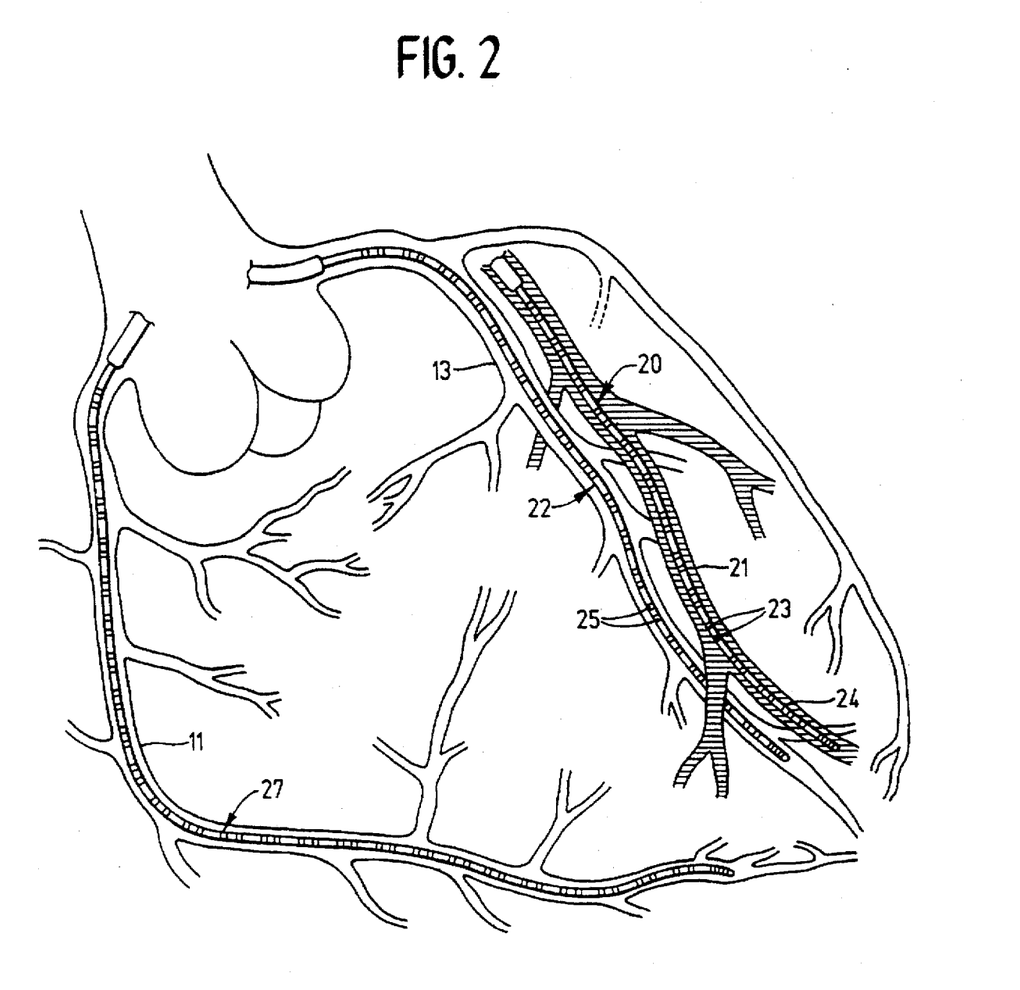
FIG. 2 is an anterior view of coronary arteries and cardiac veins of a human heart with portions of the anterior interventricular branch of the left coronary artery and the great cardiac vein in section to illustrate the intravascular devices therein.
Figure 3:
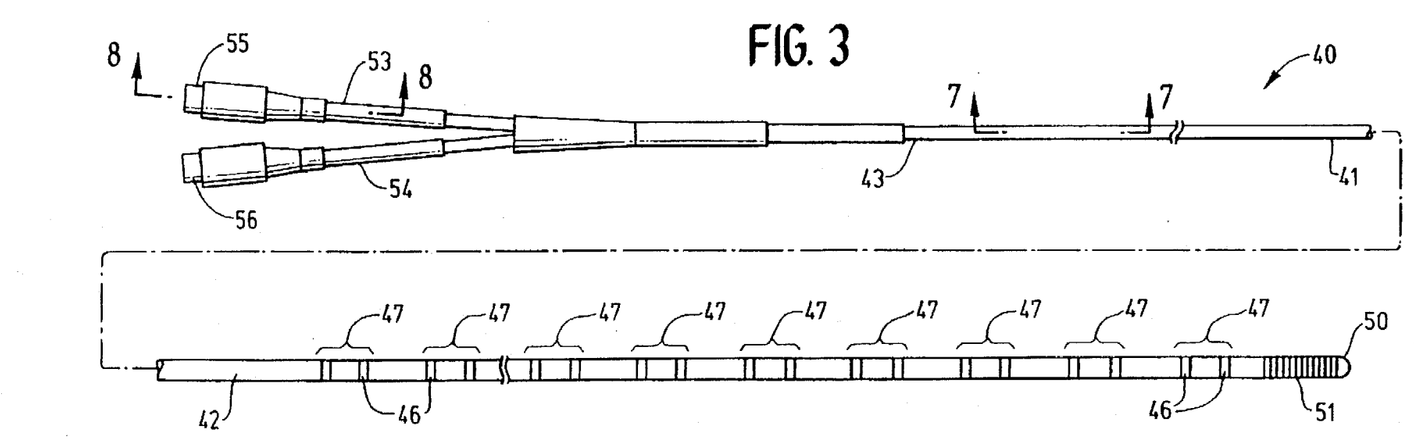
FIG. 3 is an elevational view of a guidewire embodying features of the invention.

Another method is depicted in FIG. 2 wherein one elongated intravascular sensing device 20 of the invention is disposed within the great cardiac vein 21 and another elongated intravascular sensing device 22 is disposed in the anterior interventricular branch of the left coronary artery 13. The intravascular sensing device 20 has a plurality of electrodes 23 space along the distal portion 24 thereof and the intravascular sensing device 22 has a plurality of electrodes 25 space along it distal portion 26. A third intravascular sensing device 27 might also be deployed within the right coronary artery 11 to provide for detection of electrical activity from a wider region of the patient's heart and to thereby facilitate more comprehensive mapping of the patient's heart. As in the prior method, the individual sensing devices may be moved within the arteries or veins to more accurately pinpoint the region from which the received electrical activity originates.

Figure 4:
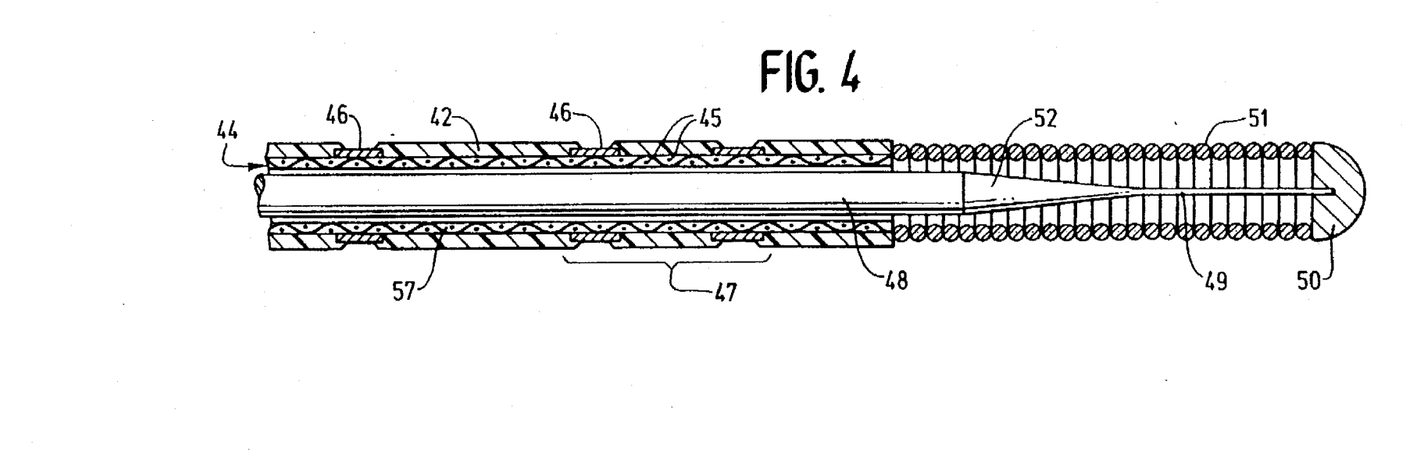
FIG. 4 is an enlarged longitudinal cross-sectional view of a distal portion of the guidewire shown in FIG. 3.

Reference is made to FIGS. 3–8 which schematically illustrate in greater detail an embodiment of the invention wherein the elongated sensing device is the form of a guidewire 40 which includes shaft 41 with a distal portion 42 and a proximal portion 43. The shaft 41 is formed of a tubular member 44 formed of a plurality of braided or woven electrical conductors 45. While it is preferable that the conductors 45 be interwoven into the tubular member 44, they may be twisted or wound about a mandrel or the core member 48. In the latter case the inner and outer layers of wires would be laid out diagonally but the conductors of one layer would be laid in the opposite direction to that of the conductors in the other layer. Usually, the wound or twisted conductors are secured together by suitable adhesive which makes the shaft relatively stiff, whereas with the interwoven conductors there is sufficient interlocking of the conductors that adhesives are not usually needed with the result of a more flexible shaft 41. The distal section 42 of the shaft 41 is provided with a plurality of electrodes 46 which are preferably arranged as pairs 47 to facilitate a bipolar or multipolar mode of operation. The core member 48 is disposed within the inner lumen of the braided tubular member 44 and extends beyond the distal end thereof. The distal end 49 of the core member 48 is preferably flattened, as shown in FIG. 4, and extends and is joined to a rounded distal tip 50 which is formed when a distal coil 51 which is disposed about the distal end of the core member is secured thereto by soldering, brazing, welding or a body of adhesive and the like. The core member 48 may be provided with one or more tapers 52 as with conventional guidewires. The proximal portion 43 of the shaft 41 has two extensions 53 and 54 which have multi-pin connectors 55 and 56 on the proximal ends thereof with each of the electrical conductors 45 being electrically connected to a separate pin.

Figure 5:
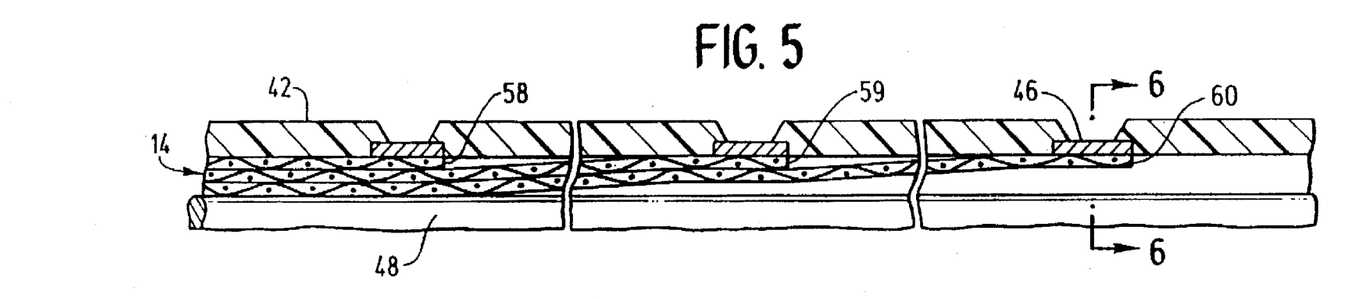
FIG. 5 is an enlarged longitudinal cross-sectional view of a distal portion of a guidewire similar to that shown in FIG. 3 but with multiple braided layers in the shaft thereof.
Figure 6:
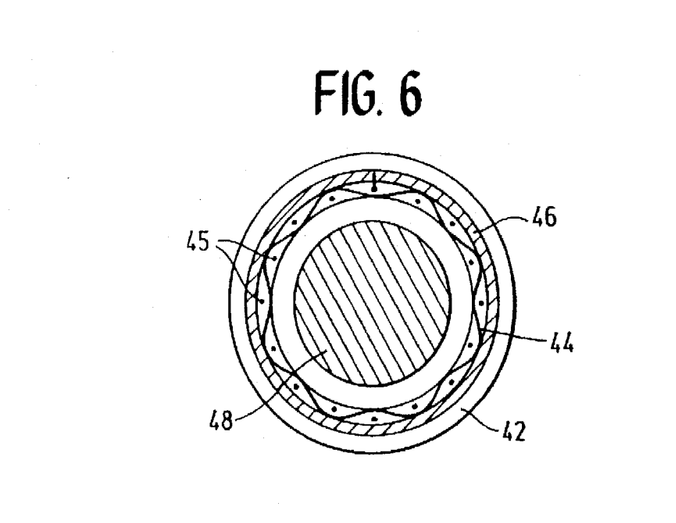
FIG. 6 is a transverse cross-sectional view of a distal portion of the guidewire shown in FIG. 5 taken along the lines 6—6.
Figure 7:
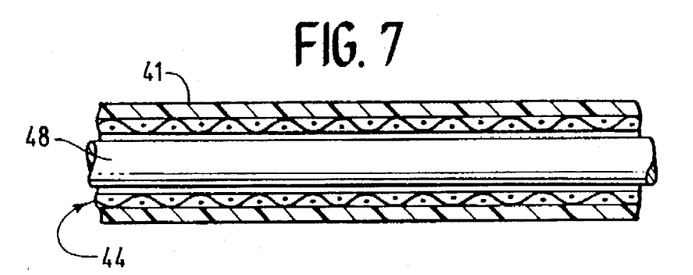
FIG. 7 is a longitudinal cross-sectional view of an intermediate portion of the guidewire shown in FIG. 3 taken along the lines 7—7.

FIG. 4 illustrates the tubular member 44 formed of a single braided layer 57 with sixteen strands. However, when a high number of electrical conductors 45 are used, e.g. more than 16, a plurality of braided layers should be employed, as depicted in FIG. 5. As shown in this drawing, the outer braided layer 58 terminates at a location proximal to that of the intermediate layer 59 and the intermediate layer terminates at a location proximal to the innermost layer 60 to facilitate securing and electrically connecting the electrodes 46 to the individual electrical conductors 45. Some of the strands in the layers may be formed of nonconductive polymer materials such as Dacron, nylon or silk.

Figure 8:
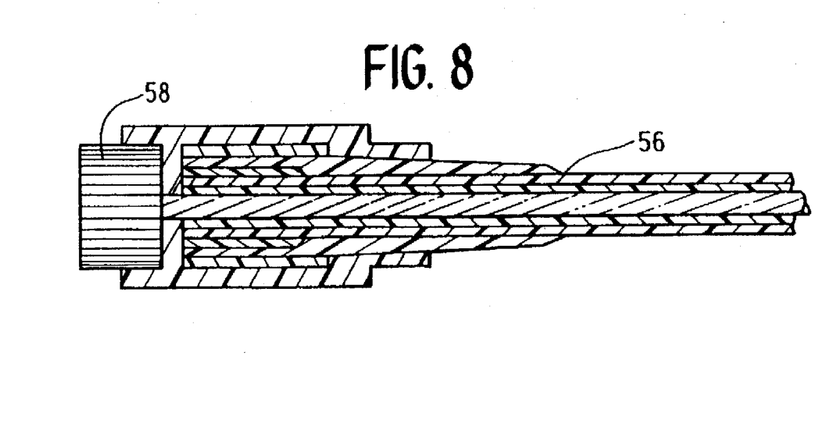
FIG. 8 is a longitudinal cross-sectional view of the an extension of the proximal end of the guidewire shown in FIG. 3 taken along the lines 8—8.

Details of proximal extension 56 is depicted in FIG. 8, wherein an sixteen pin connector 58 is schematically shown, but connectors having a higher or lower number of pins have been found suitable.

Figure 9:
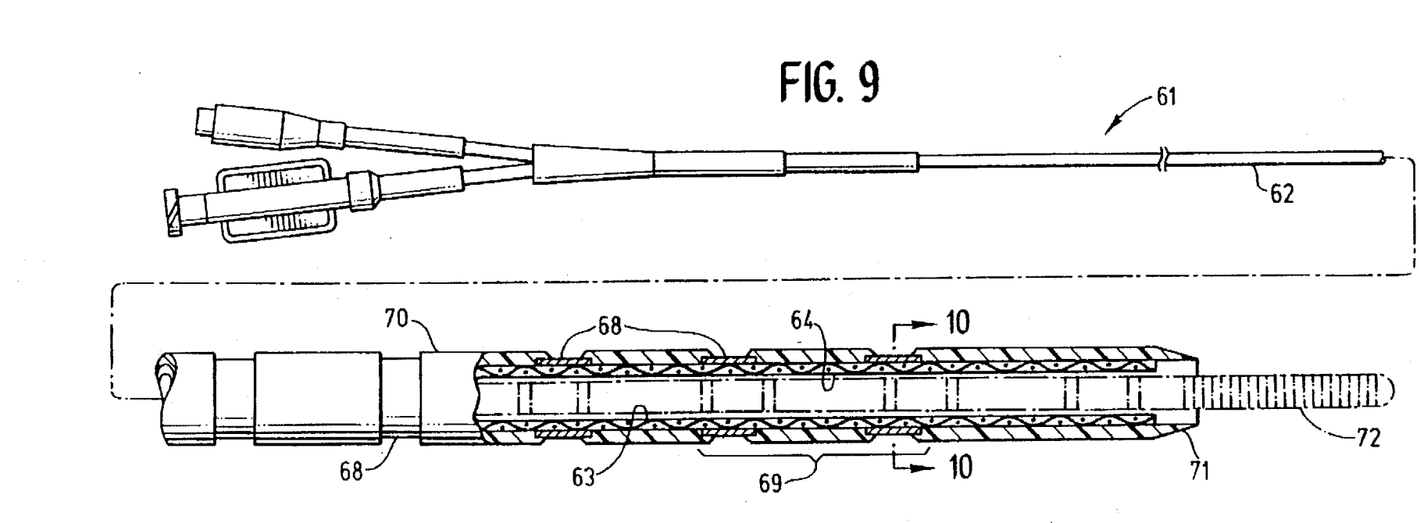
FIG. 9 is an elevational view, partially in section, of a catheter embodying features of the invention.
Figure 10:
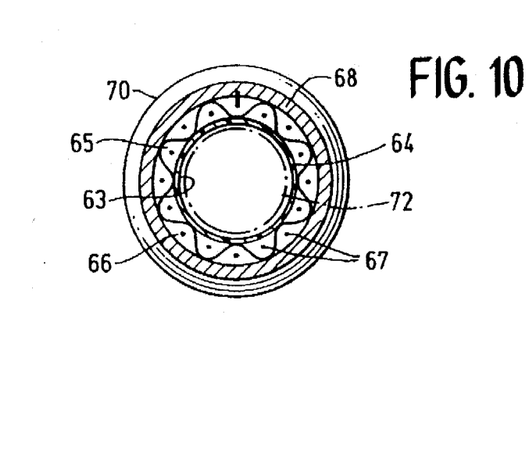
FIG. 10 is a transverse cross-sectional view of the catheter shown in FIG. 9 taken along the lines 10—10.

FIGS. 9 and 10 schematically illustrate the embodiment of the invention in the form of a catheter 61. In this embodiment, catheter shaft 62 has an inner lumen 63 defined by an inner tubular element or lining 64 which is preferably formed of lubricous material such as fluoropolymers, e.g. Teflon® and polysulfones and hydrophilic polymers such as polyvinypyrrolidone, polyethylene oxide and acrylate-based polymers. A tubular member 65 is disposed about tubular lining 64 and is formed of at least one braided layer 66. A plurality of the strands 67 making up each of the braided layers are insulated electrical conductors which are electrically connected to electrodes 68. As with the previously discussed embodiments, the electrodes 68 are preferably arranged in pairs 69 to facilitate bipolar mode operation. While not shown in the drawing, a plurality of braided layers may be desireable with more than eight electrode pairs 69. Some of the strands 67 in each of the layers may be formed of nonconducting materials such as nylon, An outer jacket 70 extends the length of the shaft 62 and the portion of the jacket extending beyond the distal end of the braided tubular member 65 is tapered to provide a nontraumatic flexible distal tip 71. As in the previously described embodiments, the outer jacket 70 overlaps the edges of the electrodes 68 to avoid exposing a sharp metal edge when advancing the catheter through a patient's blood vessel. A guidewire 72 (shown in phantom) is slidably disposed within the inner lumen 63.

The catheter 61 may also be used to direct diagnostic or therapeutic fluids to distal locations within a patients coronary vasculature. For example, fluids containing cardioplegic materials such as iced saline, solutions of KCl, lidocaine, procaineamide hydrochloride and the like can be delivered to areas of the patient's heart which are suspected to be the origin of or conduct the aberrant signals. If the arrhythmia stops upon the delivery of the cardioplegic agent, then the operator is assured that the artery or vein through which the agent is delivered leads toward or away from the area of the patient's heart which needs to be ablated in order to terminate the arrhythmia.

When using an approach to the patient's heart through the femoral artery or femoral vein, it is frequently helpful to utilize one or more guiding catheters to guide the intravascular sensing devices of the invention to the coronary artery ostium or the coronary sinus ostium. Such guiding catheters frequently have specially shaped distal tips to facilitate the seating thereof within the desired coronary ostium or coronary sinus ostium. The use of guiding catheter eliminates the need to direct the distal tip of a catheter or a guidewire of the invention into the desire ostium.

The electrodes on the distal portions of the sensing devices are typically gold bands with widths of about 0.5 mm. The distance between the electrodes of an electrode pair is typically about 1 mm and the distance between electrode pairs is typically about 7–8 mm.

The overall length of the intravascular devices of the invention depend upon the site of introduction into the patient's peripheral vasculature but may range from about 80 to about 300 cm, typically about 135 cm for delivery through the femoral artery or vein and about 90 cm for delivery through the brachiocephalic artery or internal jugular vein. The flexible distal portions of the intervascular sensing devices are about 10 to about 50 cm in length and are configured to be readily advanceable through a patient's coronary arteries or cardiac veins. The outer diameter of the catheter form of the sensing device should be less than about 0.055 inch (1.4 mm) and preferably about 0.035 inch (0.89 mm) and the inner lumen thereof is about 0.012 to about 0.022 inch (0.3–0.56 mm) in diameter to facilitate the reception and advancement of a guidewire therethrough. The distal portion of the guidewire is about 15 to about 40 cm in length and about 0.008 to about 0.022 inch (0.2–0.56 mm) in outer diameter to facilitate advancement through blood vessels having native diameters of less than 1 mm, frequently less than 0.75 mm. The distal coil on the guidewire is about 2 to about 10 cm in length and is formed of wire about 0.0003 to about 0.006 inch (0.0076–0.15 mm) in diameter. It is preferably formed of platinum to facilitate fluoroscopic observation thereof within the patient, but it may be formed in whole or in part with other material such as stainless steel, titanium, palladium, niobium, iridium, rhodium and alloys thereof.

Figure 11:
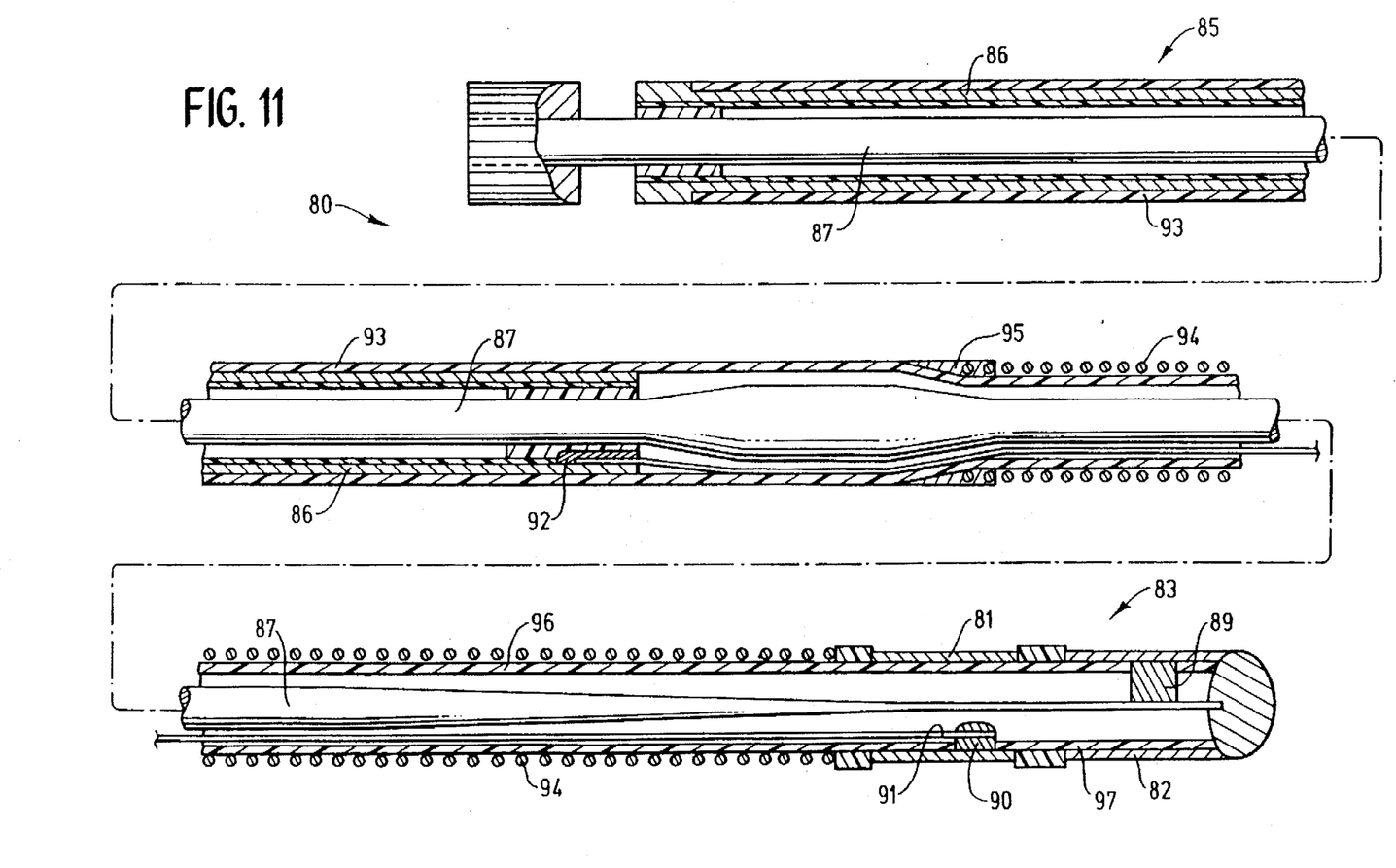
FIG. 11 is a longitudinal cross-sectional view of alternative guidewire suitable for use with the present invention.

To the extent not previously described, the materials of construction of the various guidewire and catheter parts may be formed of conventional materials. The electrical conductors may be electrical grade copper wire about 0.005 inch (0.127 mm) in diameter which are provided with a thin insulated jacket or coating of polyimide or other suitable insulator. The outer jacket may be a thermoplastic fluoropolymer such as THV which is available from 3M Corporation. The core wire of the guidewire may be formed of stainless steel or a superelastic NiTi type alloy, the latter exhibiting a stable austenite phase at body temperature. Preferably, the NiTi alloy exhibits a stress induced transformation from the stable austenite to a lower strength martensite phase. Upon release of the stress, the alloy returns to the austenite phase. Proximal and distal sections of the core member may be formed of different materials so as to provide a stronger proximal section for greater pushability and a more flexible distal section to facilitate passage through tortuous coronary anatomy. Manufacturing techniques used in making catheters and guidewires for angioplasty procedures may be used in the making of the intravascular devices of the invention. An alternative embodiment of the invention in the form of a guidewire 80 is shown in FIG. 11 which is similar to that shown in FIGS. 3–8 except that only a single pair of electrodes 81 and 82 are shown on distal portion 83. The shaft 84 has a proximal portion 85 which is formed in part of a hypotube 86. A core member 87 extends through the inner lumen of the hypotube 86 and is electrically isolated from the hypotube 86 by insulating jacket 88. The distal portion of the core member 87 extends out the distal end of the hypotube 86 as indicated in the drawing. The distal electrode 82 is electrically secured to the core member 87 by solder 89 and the proximal electrode 81 is secured by solder 90 to electrical conductor 91 which may be an insulated wire or ribbon. The proximal end of the electrical conductor 91 is secured by solder 92 to the hypotube 86 which is formed of electrically conductive metal (stainless steel). The exterior surface of the conductive metal tube 86 should be provided with an insulating jacket or coating 93. The core member 87 and the conductive metal tube 86 are preferably secured together at one or more locations by an insulating adhesive to facilitate the torqueability of the overall guidewire shaft. Preferably, they are secured at least at the distal end of the metal tube 86.

A coil 94 is disposed about the distal portion of the core member 87 proximal to the proximal electrode 81 and it is secured to the core member by a suitable means 95. Such securing may be effected by soldering, brazing, welding or suitable adhesive depending upon the materials from which the coil 94 and the core member 87 are made. The core member 87 and the coil 94 provide shapeability to the distal portion 83 of the guidewire 80 to facilitate its advancement into side branches of a patient's vasculature.

An inner tubular member 96 may be disposed within the coil 94 in the distal section 83 to provide support to the electrode 81 and inner tubular member 97 may be disposed within the coil 94 to likewise provide support thereto to electrode 82. A suitable material is thin walled polyimide tubing which is frequently mentioned as being suitable for use in intravascular catheters.

Figure 12:
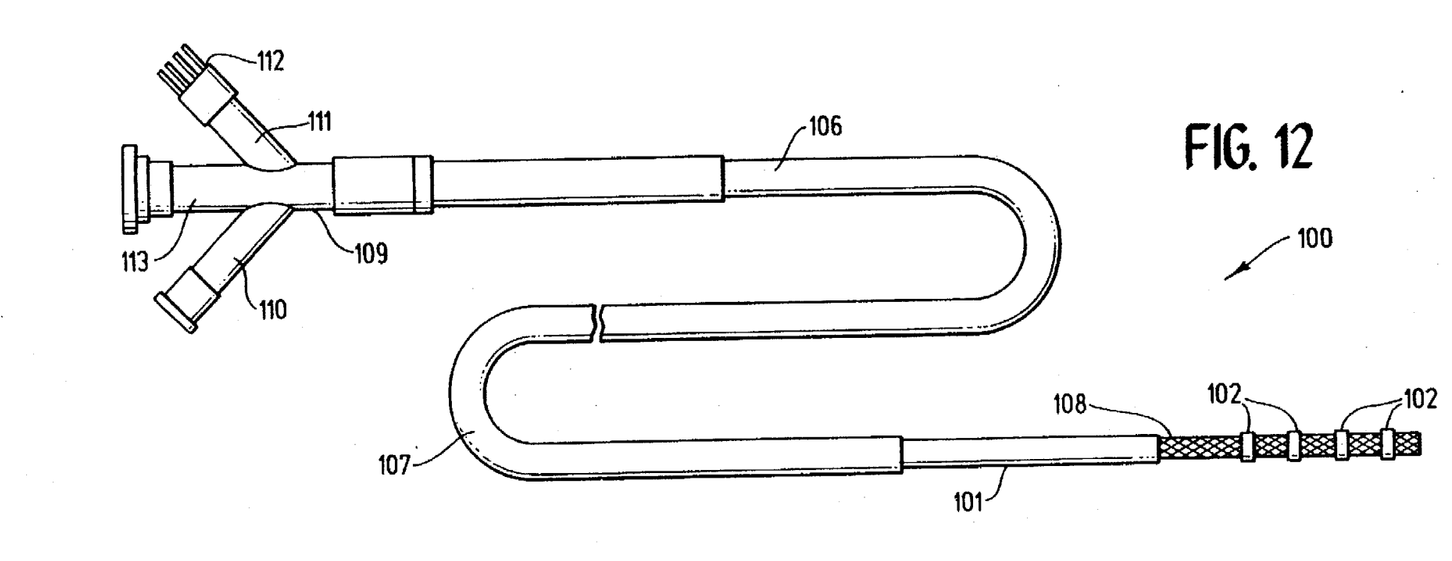
FIG. 12 is an elevational view, partially in section, of a catheter system suitable for use with the present invention.
Figure 13:
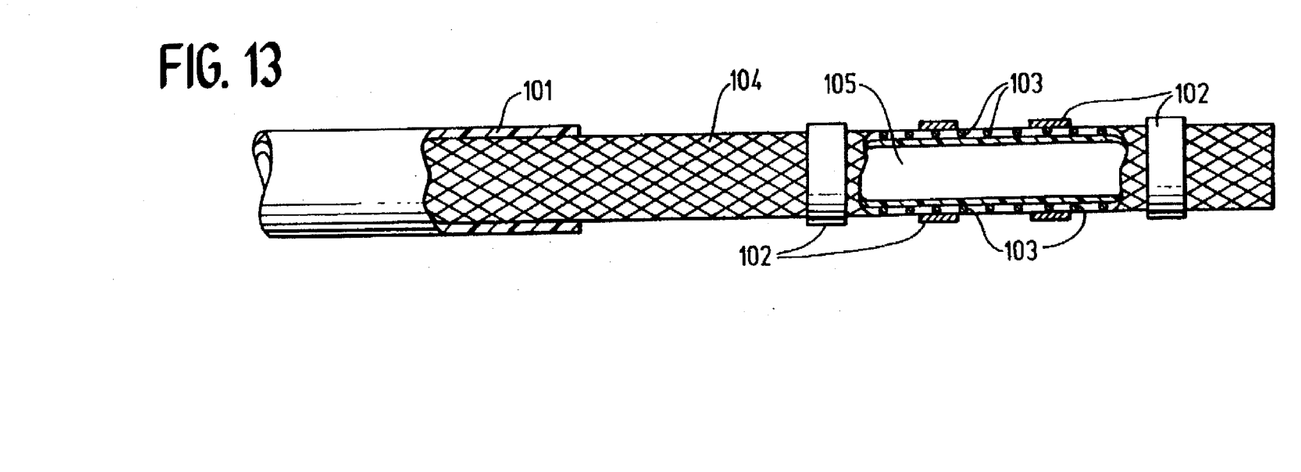
FIG. 13 is an enlarged elevational view, partially in section, of the distal portion of the catheter shown in FIG. 12.

FIGS. 12 and 13 illustrate a catheter assembly 100 which embodies an additional aspect of the present invention directed to an intravascular catheter 101 for sensing electrical activity within a patient's coronary or cardiac blood vessels. As shown in FIG. 13 electrodes 102 are electrically connected to individual electrical conductors 103 which are woven or wound to form the tubular shaft 104 of the catheter 101. All of the strands which are wound to form the shaft 104 need not be conductors 103 as in the prior embodiments, and when there are more than 16 electrodes and thus more than 16 electrical conductors, multiple woven layers may be employed. The electrical conductors 103 are typically electrical grade copper wires of suitable outer diameter such as about 0.004 to about 0.01 inch (0.10–0.25 mm). The conductors 103 may be formed of other conducting materials such as silver, gold and platinum. A suitable insulating material to coat the conductors 103 is polyimide which minimizes cross talk and which can be applied in very thin layers. As in the other embodiments of the invention the conductors 103 may be woven or merely wound, but preferably are woven.

The inner lumen 105 of the catheter 100 is configured to slidably receive a guidewire to facilitate the advancement of the catheter over the guidewire and preferably has at least in the distal portion thereof a diameter about 0.002 to about 0.005 inch (0.051–0.127 mm) greater than the guidewire which is to be disposed therein. For guidewire having OD of about 0.016 to about 0.018 inch (0.41–46 mm), the inner lumen 97 would be about 0.018 to about 0.023 inch (0.46–0.58 mm). The OD of the catheter may range from about 0.03 to about 0.1 inch (0.76–2.54 mm) but preferably is about 0.03 to about 0.05 inch (0.076–1.27 mm, particularly 0.035 to about 0.040 inch (0.89–1.02 mm).

The proximal portion 106 of the catheter 100 makes up about 70 to about 95% of the total length of the catheter with the intermediate portion 107 and the distal portion 108 which has the sensing electrodes 102 being the remainder. Preferably the catheter 100 has decreasing stiffness from the proximal portion 106 to the intermediate portion 107 and the distal portion 108 to facilitate the advancement of the catheter 100 within the patient's vasculature. The exterior surface of the catheter 100 and the surface defining inner lumen 105 are formed of lubricous materials or hydrophilic materials which become lubricous when contacting aqueous based fluids. Polysulfones and polyfluoroalkanes are examples of suitable lubricous polymers and polyvinypyrrolidone, polyethylene oxide and acrylate-based polymers of examples of suitable hydrophilic polymers.

The proximal end of the catheter 106 may be provided with a multiple arm adapter 109 as shown in FIG. 12 with one arm 110 which is configured to receive a syringe for delivering fluid into the inner lumen and a second arm 111 which is provided with an electrical connector 112 which is electrically connected to the electrical conductors 103. The central arm 112 facilitates entry of a guidewire (not shown) into the inner lumen 105.

Once the arrhythmogenic site or conductive pathway causing an arrhythmia is located by detecting the electrical activity, The guidewire may be removed and means can be advanced through the inner lumen 105 of a catheter of the invention to occlude an arterial passageway which feeds the arrhythmogenic site or conductive pathway so as to terminate the arrhythmia.

Figure 14:
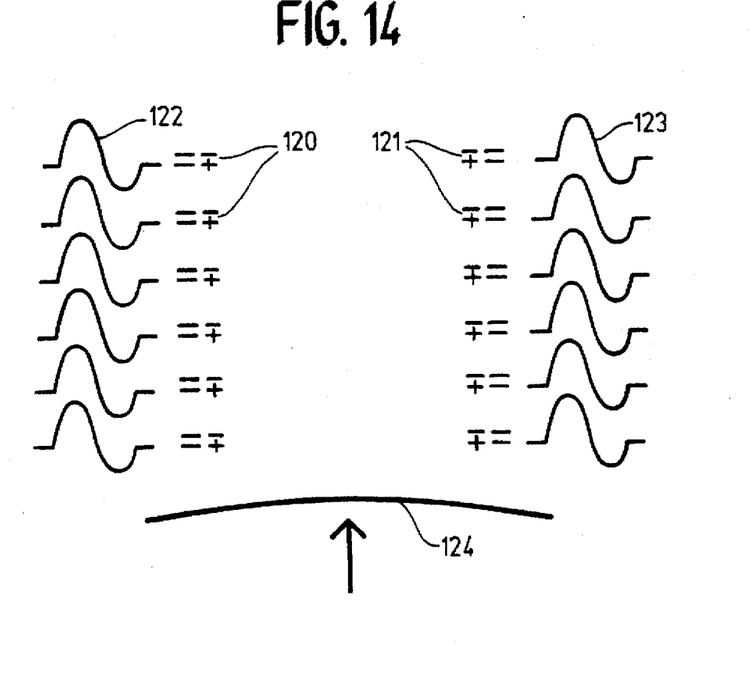
FIG. 14 is a schematic view of a wave front passing on end to a pair of intravascular sensing devices with a plurality of bipolar electrodes and the response from the passage of the wave front through each electrode pair.

FIG. 14 schematically represents the output from a plurality of electrode pairs 120 and 121 on separate intravascular devices (not shown) disposed in different, generally parallel coronary blood vessels, e.g. a coronary artery and the companion vein to a nearly planar wave front approaching on end to the intravascular devices. The bipolar response 122 and 123 to the wave front 124 from each electrode pair is shown adjacent thereto, and as indicated, all of the responses are essentially identical, except for the time-of-occurrence, because the wave front 124 reaches all of the electrodes at the same angle. Changes in tissue properties adjacent the catheters may retard the passage of the wave front and may distort the shape of the output.

Figure 15:
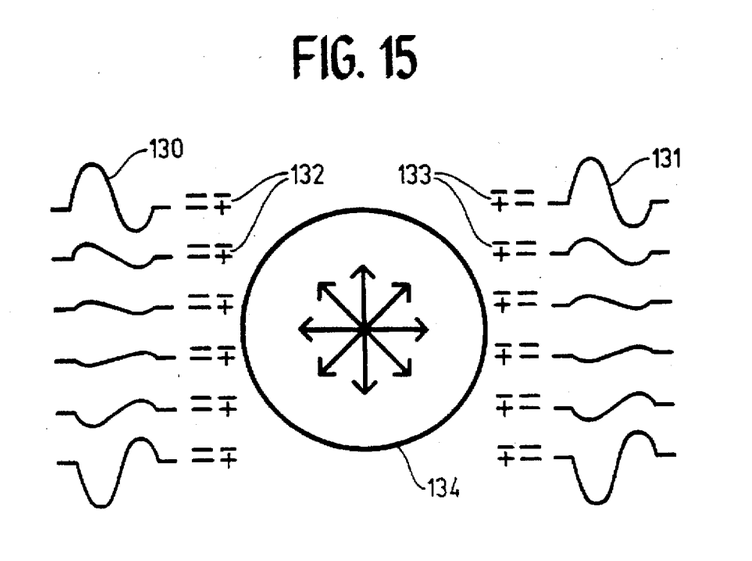
FIG. 15 is a schematic view of a wave front emanating from a source between two intravascular sensing devices with a plurality of bipolar electrodes and the response from the passage of the wave front through each electrode pair.

FIG. 15 schematically represents the responses 130 and 131 from a plurality of electrode pairs 132 and 133 on separate intravascular devices (not shown) disposed in different generally parallel coronary blood vessels, as in FIG. 14, but the wave front 134 originates from an arrhythmogenic site between and in close proximity to the catheters. The wave front 134 is circular (idealized) and the size and polarity of the responses to the expanding wave front varies according to the angle of incidence.

The time of occurrence and the directional information in the aforementioned schematic drawings may be used to determine the origin of the ectopic beat.

The present invention has been described herein in terms of certain preferred embodiments but various modifications and improvements may be made to the present invention without departing from the scope thereof.

What is claimed is:

1. A method for detecting electrical activity within a patient's body comprising:

a) introducing into the vasculature of a patient's body a first intravascular device which includes
   an elongated shaft having proximal and distal ends, a port in the distal end, an inner lumen extending therein in communication with the port in the distal end and a plurality of electrical conductors extending from a distal portion of the shaft to a proximal portion thereof, and
   a plurality of sensing electrode pairs situated on the distal portion of the shaft, each sensing electrode of a plurality of electrode pairs being electrically connected to a separate electrical conductor to facilitate a bipolar operative mode;
 b) introducing into the vasculature of the patient's body a second intravascular device longer than the first device which is slidably disposed within the inner lumen of the first intravascular device, which is configured to extend through the port in the distal end of the first intravascular device and which includes
   an elongated shaft having a plurality of electrical conductors extending from a distal portion to a proximal portion thereof, and
   a plurality of sensing electrode pairs situated on the distal portion of the shaft of the second intravascular device, each sensing electrode of a plurality of electrode pairs being electrically connected to a separate electrical conductor to facilitate a bipolar operative mode;
 c) moving the first and second intravascular devices within the patient's vasculature so that the distal portion of the first device is positioned therein with the electrodes thereon at a first desired intravascular location and the distal portion of the second intravascular device extending out the port in the distal end of the first intravascular device with the electrodes thereon at a second desired intravascular location distal to the first intravascular location; and
 d) detecting electrical activity by means of a plurality of electrode pairs on both the first and second intravascular devices in a bipolar mode.

2. The method of claim 1 including further moving one of the first or second intravascular devices so that the distal portion of the further moved device is positioned at a third desired intravascular location.

3. The method of claim 2 including detecting electrical activity by means of electrodes on the distal portion of the further moved intravascular device.

4. The method of claim 2 wherein the intravascular locations are within the patient's coronary arteries.

5. The method of claim 4 wherein the coronary artery is an artery selected from the group consisting of the left coronary artery, the right coronary artery, the marginal artery, the interior interventricular artery and the circumflex artery.

6. The method of claim 2 wherein the intravascular locations are within the patient's cardiac veins.

7. A system for detecting electrical activity from within a blood vessel of a patient's body comprising:

a) a first intravascular device which includes
   a first elongated shaft having proximal and distal ends, a port in the distal end, an inner lumen extending therein to and in communication with the port and a plurality of electrical conductors extending from a distal portion of the first shaft to a proximal portion thereof, and
   a plurality of sensing electrode pairs situated on the distal portion of the first shaft, each sensing electrode of a plurality of sensing electrode pairs being electrically connected to a separate electrical conductor to facilitate a bipolar operative mode;
 b) a second intravascular device which is slidably disposed within the inner lumen of the first intravascular device, which is configured to extend out the port in the distal end of the first intravascular device and which includes
   a second elongated shaft having proximal and distal ends, a plurality of electrical conductors extending from a distal portion to a proximal portion thereof, and
   a plurality of sensing electrode pairs situated on the distal portion of the second shaft, each sensing electrode of a plurality of said sensing electrode pairs being electrically connected to a separate electrical conductor to facilitate a bipolar operative mode.

8. The system of claim 7 wherein the distal portions of the first and second intravascular devices have flexibilities and outer diameters with dimensions suitable to facilitate advancement within the patient's coronary blood vessels.

9. The system of claim 8 wherein the distal portion of the first intravascular device has an outer diameter of not greater than 0.05 inch.

10. The system of claim 8 wherein the distal portion of the first intravascular device has an outer diameter of not greater than 0.04 inch.

11. The system of claim 8 wherein the distal portion of the second intravascular device has an outer diameter of not greater than 0.02 inch.

12. The system of claim 8 wherein the inner lumen in the distal portion of the first intravascular device has a diameter which is about 0.002 to about 0.005 inch greater than the outer diameter of the distal portion of the second intravascular device.

13. The system of claim 7 wherein the electrodes on the first and second intravascular devices have interelectrode spacings of about 1 to about 10 mm.

14. The system of claim 13 wherein the electrodes are cylindrically shaped bands.

15. The system of claim 14 wherein the electrodes are at least about 0.005 inch in width.

16. The system of claim 7 wherein the plurality of electrical conductors of the first intravascular device are individually insulated and woven to form the shaft thereof.

17. The system of claim 7 wherein each of the plurality of electrical conductors are a plurality of flat electrical conductors are wound spirally around a core wire in a number of layers.

18. The system of claim 7 wherein each of the first and second intravascular devices have electrical junctions at their proximal ends.

19. The system of claim 7 wherein the second intravascular device has a coil tip on a distal extremity thereof.

20. The system of claim 7 wherein the second intravascular device has a exterior covering formed of plastic selected from the group consisting of fluorinated polymers, polyethylene, polypropylene, polybutene, polyurethane, and their mixtures and copolymers, hydrophilic polymers including polyvinylpyrrolidone, polyethylene oxide, and hyaluronic acid polymers.

21. The system of claim 7 wherein the distal portion of the first intravascular device is much shorter and more flexible than the proximal portion thereof.

22. The system of claim 7 wherein the distal portion of the second intravascular device is much shorter and more flexible than the proximal portion thereof.

23. A catheter assembly for detecting electrical activity within a blood vessel of a patient's heart comprising:
a) an intravascular catheter having
a first elongated shaft having proximal and distal ends, an inner lumen extending therein, a port on the distal end in communication with the inner lumen and a plurality of electrical conductors extending from a distal portion of the first shaft to the proximal end thereof, and
a plurality of sensing electrode pairs mounted on the distal portion of the first shaft, each sensing electrode of a plurality of said sensing electrode pairs being electrically connected to a separate electrical conductor to facilitate a bipolar operative mode; and
b) an intravascular guidewire longer than the intravascular catheter, configured to extend out the port in the distal end of the intravascular catheter, slidably disposed within the inner lumen of the catheter and having
a second elongated shaft having proximal and distal ends, a plurality of electrical conductors extending from a distal portion of the shaft to the proximal end thereof, and
a plurality of sensing electrode pairs mounted on the distal portion of the second shaft, each sensing electrode of a plurality of electrode pairs being electrically connected to a separate electrical conductor to facilitate a bipolar operative mode.

24. The catheter assembly of claim 23 wherein the electrical conductors of the intravascular catheter are electrically connected to separate pins of an electrical connector.

25. The catheter assembly of claim 23 wherein an adapter on the proximal end of the catheter shaft has means to introduce fluid into the inner lumen which extends within the catheter shaft.

26. The catheter assembly of claim 23 wherein the first shaft is formed at least in part of a plurality of the electrical conductors which are individually insulated and wound or braided into a tubular structure.

27. The catheter assembly of claim 26 wherein the tubular structure has a plastic jacket on an exterior portion thereof.

28. The catheter assembly of claim 26 wherein the tubular structure includes an inner tubular element which defines the inner lumen and about which the electrical conductors are wound or braided.

29. A method of detecting electrical activity within a cardiac vein or a coronary artery of a patient's heart, comprising:
a) providing within a cardiac vein or a coronary artery of a patient's heart an intravascular catheter which has
an elongated catheter shaft having proximal and distal ends, a port in the distal end, an inner lumen extending therein to and in fluid communication with the port in the distal end, and electrical conductors extending from a distal portion of the catheter shaft to the proximal end thereof, and
a plurality of sensing electrode pairs mounted on the distal portion of the catheter shaft with each electrode of a plurality of electrode pairs being electrically connected to a separate electrical conductor;
b) providing within the cardiac vein or the coronary artery of the patient's heart an intravascular guidewire which is slidably disposed within the inner lumen of the catheter shaft, which is configured to extend out the port in the distal end of the intravascular catheter and which has
an elongated guidewire shaft having proximal and distal ends and electrical conductors extending from a distal portion of the guidewire shaft to the proximal end thereof, and
a plurality of sensing electrode pairs mounted on the distal portion of the guidewire shaft with each sensing electrode of a plurality of electrode pairs being electrically connected to a separate electrical conductor to facilitate a bipolar operative mode;
c) detecting electrical activity of the patient's heart from within the cardiac vein or the coronary artery by means of a plurality of electrode pairs on the intravascular catheter and a plurality of electrode pairs on the intravascular guidewire.

30. A method of detecting electrical activity at a plurality of intravascular locations within a patient's heart to facilitate the mapping thereof, comprising:
a) advancing to a first intravascular location within a first coronary artery or a cardiac vein of a patient's heart a first intravascular device which includes
a first elongated shaft having a plurality of electrical conductors extending from a distal portion of the first shaft to a proximal portion thereof, and
a plurality of sensing electrode pairs situated on the distal portion of the first shaft, each sensing electrode of a plurality of electrode pairs being electrically connected to a separate electrical conductor to facilitate a bipolar operative mode;

b) advancing to a second intravascular location within a second coronary artery or cardiac vein of the patient's heart different from the first mentioned coronary artery or cardiac vein a second intravascular device which includes
- a second elongated shaft having a plurality of electrical conductors extending from a distal portion to a proximal portion thereof, and
- a plurality of sensing electrode pairs situated on the distal portion of the shaft, each sensing electrode of a plurality of electrode pairs being electrically connected to a separate electrical conductor to facilitate a bipolar operative mode; and c) detecting electrical activity by means of said electrode pairs on both the first and second intravascular devices at the first and second intravascular locations respectively in bipolar operative modes.

31. The method of claim 30 including changing the relative positions of the first and second intravascular devices within the cardiac vein or the coronary artery of the patient's heart; and detecting the electrical activity of the patient's heart from within the cardiac vein or the coronary artery by means of electrode pairs on both of the intravascular devices.

* * * * *